United States Patent [19]

Azoulay

[11] 4,400,466
[45] Aug. 23, 1983

[54] PROCESS FOR THE PREPARATION OF VISCOUS WATER BY ACTION OF MICRO-ORGANISMS

[75] Inventor: Edgard E. Y. Azoulay, Marseilles, France

[73] Assignee: Dumas & Inchauspe, Pau, France

[21] Appl. No.: 312,165

[22] Filed: Oct. 16, 1981

[30] Foreign Application Priority Data

Oct. 17, 1980 [FR] France ............................ 80 22210

[51] Int. Cl.³ .......................... C12P 19/04; C12R 1/41
[52] U.S. Cl. ................................... 435/101; 435/261; 435/878
[58] Field of Search ............... 435/101, 102, 103, 104, 435/813, 878, 261

[56] References Cited

U.S. PATENT DOCUMENTS

| | | | |
|---|---|---|---|
| 3,251,749 | 5/1966 | Lipps | 195/31 |
| 3,328,262 | 6/1967 | Lindblom et al. | 195/31 |
| 3,406,114 | 10/1968 | Goren | 435/103 X |
| 3,485,719 | 12/1969 | Rogovin | 435/104 |
| 3,856,626 | 12/1974 | Clamen et al. | 435/101 |
| 4,218,538 | 8/1980 | Church | 435/101 |

*Primary Examiner*—Arnold Turk
*Attorney, Agent, or Firm*—Fleit, Jacobson & Cohn

[57] ABSTRACT

Viscous water for use in oil extraction is produced continuously by bacterial action. A carbohydrate substrate, nitrogen-containing mineral salts and growth factors are introduced into a first fermenter chamber containing bacteria of the genus Rhizobium capable of excreting polysaccharides having viscosity increasing properties and aqueous product, from which the bacteria are separated, is collected from the outlet of this chamber and recycled to the inlet of chamber. Into a second viscosifier chamber there is introduced carbohydrate substrate for synthesis of polysaccharide and bacteria recovered from the first chamber in an amount approximately equal to that which is removed with the viscous product from the second chamber and there is collected from the outlet of the second chamber the viscous product at a rate approximately equal to that of the carbohydrate substrate at the inlet in order to maintain equilibrium in the system.

8 Claims, 1 Drawing Figure

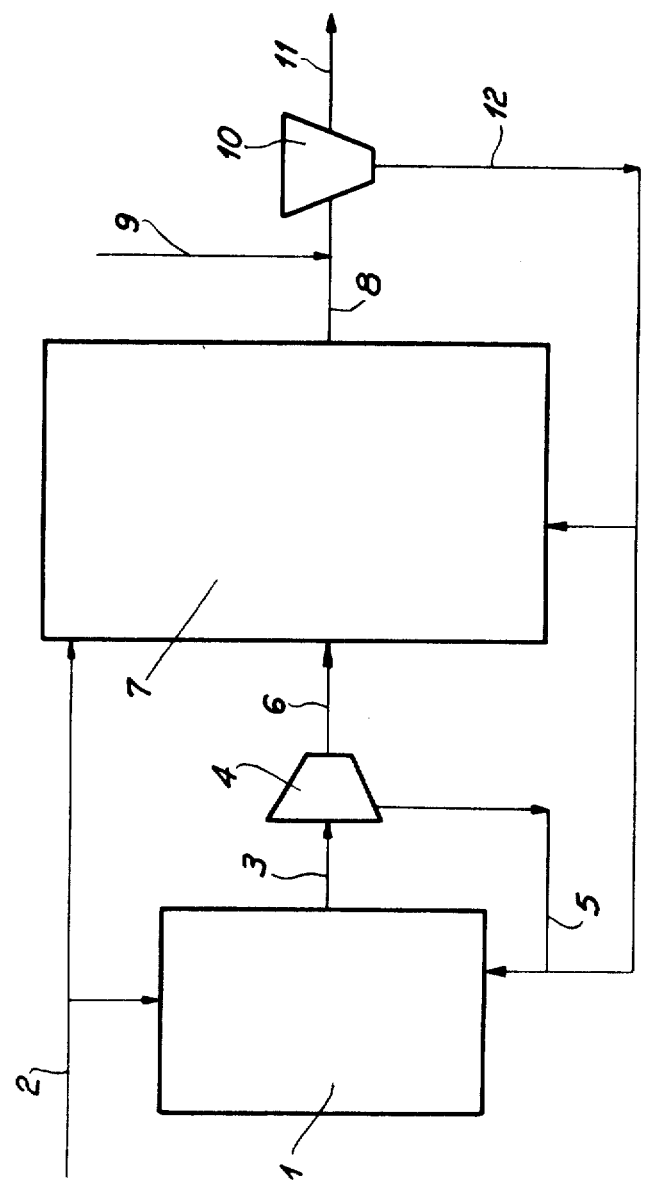

PROCESS FOR THE PREPARATION OF VISCOUS WATER BY ACTION OF MICRO-ORGANISMS

BACKGROUND OF THE INVENTION

The present invention relates to a process of preparation of viscous water as well as to the viscous water produced by this process. This water is principally used in oil extraction.

Many processes are already known for maintaining oil wells in active service; amongst these there can be mentioned that comprising injecting viscous water into the wells. Viscous water is so-called due to the fact that there are added to the water, salted or not, thickening agents such as polyacrylamides, which are petrochemical products, or xanthan gums.

These last are provided from the fermentation of carbon-containing substrates by bacteria of the species Xanthomonas according to the process first described in U.S. Pat. No. 3,000,790 and then improved on in numerous U.S. Pat. Nos. 3,020,206, 3,391,060, 3,427,226, 3,433,708, 3,271,267, 3,251,749, 3,281,329, 3,455,760, 3,565,763, 3,594,280 and 3,391,061. The use of viscous solutions of xanthan gums in the recovery of oil is described in numerous U.S. Pat. Nos. 3,243,000, 3,198,268, 3,532,166, 3,305,016, 3,251,417, 3,391,060, 3,319,715, 3,373,810, 3,434,542, 3,729,460, 3,853,771, 4,010,071 and 4,119,546.

It is to be noted that all this literature treats in diverse fashion the use or improvement of the xanthan gums obtained in a discontinuous operation which extends generally for two to four days during which bacteria of the species Xanthomonas campestries are fermented on carbohydrate substrates such as molasses, by-products of the sugar industry, or glucose syrup resulting from the hydrolysis of starch. On the other hand, U.S. Pat. No. 3,965,985 describes a process, also discontinuous, for obtaining viscous water, which uses various micro-organisms capable of fermenting oxygenated compounds of petroleum fractions, such as aldehydes or methanol.

The discontinuous production of a chemical or biochemical product is much more onerous than continuous production and up to now the high cost of xanthan gums produced by discontinuous fermentation has in practice prohibited their use in assisting oil recovery, despite all the improvements imparted to this product by the references cited above. Therefore the essential aim of the present invention is a process for preparing viscous water in continuous fashion, that is to say cheaply.

Another aim of the invention is the use of genera of bacteria other than the Xanthomonas using the same carbohydrate substrates, sugars, glucose or starch hydrolysates.

Another aim of the invention is a process of this type which can be put into operation near oilfields. An object of the invention is a viscous water prepared according to such a process having properties equal to or superior to those prepared by the previously known processes.

DESCRIPTION OF THE INVENTION

These aims and this object, as well as others which will appear in the following, are obtained by the process according to the present invention, which permits production of viscous water by bacterial action and comprises the following steps:

(a) introducing into a first chamber (called a fermenter) containing a bacterial strain of the genus Rhizobium capable of excreting polysaccharides having viscosity increasing properties, a carbohydrate substrate, nitrogeneous material in the form of mineral salts, and growth factors;

(b) collecting from the outlet of this first chamber an aqueous product from which the bacteria are separated;

(c) introducing into a second chamber (called a viscosifier), by a first inlet, the bacteria recovered in step (b) and, by a second outlet, a carbohydrate substrate providing the raw material for synthesis of the polysaccharides;

(d) collecting from the outlet of said second chamber a viscous product at the rate approximately equal to that of the carbohydrate substrate at the inlet of this second chamber, called viscosifier;

(e) optionally diluting the viscous product recovered from step (d) with water in proportions appropriate to the envisaged use.

Advantageously during step (b) the bacteria of the aqueous product collected are separated by centrifugation and this aqueous product substantially free from bacteria is recycled to step (a).

Preferably, the process further comprises the following step;

(f) recovering by physical separation the bacteria entrained in the product collected in step (d) and recycling them to step (c) or step (a).

Advantageously the physical separation of the step (f) is centrifuging.

Preferably, the same carbohydrate substrate is introduced in stages (a) and (c).

Advantageously this carbohydrate substrate is chosen from the group constituted by the hexoses such as glucose, sucrose, fructose or their mixture or also manioc, corn and other starchy products or their hydrolysates.

Advantageously, the bacterial strain is chosen from the group constituted by *Rhizobium meliloti, Rhizobium leguminosarum, Rhizobium phaesoli, Rhizobium trifoli, Rhizobium japonicum* and *Rhizobium lupini.*

Preferably, the bacterial strain is *Rhziobium meliloti.*

The present invention extends also to the viscous water thus obtained by this process and to its use in oil extraction.

The description, which follows and which is nonlimiting in character, must be read together with the accompanying drawings which schematically represents a summary of the process according to the present invention.

Into a first chamber called fermenter 1 containing a bacterial strain which is capable of excreting polysaccharides having viscosity increasing properties, there is introduced a carbon-containing substrate 2. As example of such a strain, there may be mentioned those of the genus Rhizobium such as *Rhizobium meliloti, Rhizobium leguminosarum, Rhizobium phaesoli, Rhizobium trifoli, Rhizobium japonicum* and *Rhizobium lupini.* Notably the strain *Rhizobium meliloti* is particularly suitable.

Likewise there are introduced into the fermenter 1 nitrogeneous materials in the form of mineral salts and growth factors in a manner favouring the multiplication, that is to say the fermentation, of the bacterial cells.

By way of example of the fermentation media there may be mentioned those of the following composition:

| | | | | |
|---|---|---|---|---|
| $K_2HPO_4$ | 1 | g/l | 5 | g/l |
| $KH_2PO_4$ | 1 | g/l | 1 | g/l |
| $KNO_3$ | 0.6 | g/l | — | |
| $(NH_4)_2SO_4$ | — | | 2 | g/l |
| NaCl | — | | 0.5 | g/l |
| $MgSO_4.7H_2O$ | 0.25 | g/l | 0.2 | g/l |
| $FeCl_3.6H_2O$ | 0.01 | g/l | 0.02 | g/l |
| $CaCl_2.2H_2O$ | 0.15 | g/l | 0.05 | g/l |
| Biotin | 0.20 | g/l | 0.25 | mg/l |
| Thiamine | — | | 0.1 | mg/l |
| Carbohydrate substrate | 10 | g/l | 10 | g/l |
| Water | | | up to 1 liter | |

The carbohydrate substrate may be of glucose, or of other hexoses, mannitol, sorbitol, soluble starch or corn. The biotin and thiamine may be used in the form of yeast extracts or any other source of soluble vitamins.

This chamber 1 is maintained under aerobic conditions, at a temperature of about 32° C. and the pH of the medium is approximately neutral.

At the outlet of this stage (a) of fermentation, there is collected an aqueous product 3 comprising the bacteria and the fermentation medium. These two constituents are separated for example by means of a centrifuge 4: the fermentation medium 5 is recycled to the fermenter 1, while the bacteria 6 are introduced into the second chamber, called viscosifier 7.

Independently of the bacteria 6, there is added to the viscosifier 7 a carbon-containing substrate which is, according to the preferred method of carrying out the invention, the same as that introduced into the fermenter 1. On the other hand, there is not introduced any nitrogeneous material nor any growth factor. Thus the medium contained in the viscosifier 7 has for example one of the following compositions:

| | | | | |
|---|---|---|---|---|
| $Mg SO_4.7H_2O$ | 0.2 | g/l | 0.2 | g/l |
| $K_2HPO_4$ | 1 | g/l | 9 | g/l |
| $KH_2PO_4$ | — | | 1 | g/l |
| Carbohydrate substrate | 10 | g/l | 20 | g/l |

The pH of the medium is maintained at about 7.6 with a normal solution of potash.

The cellular concentration in the viscosifier 7, which is maintained at approximately 32° C. and under aerobic conditions, comprises between 1.5 and 4.30 g/l with regard to the medium.

The bacteria in the presence of the carbon-containing substrate 2 synthesize polysaccharides, which show themselves by an increase in the viscosity of the medium.

At the outlet of step (c) of viscosity increase, a viscous product 8 is collected.

In order that the process according to the present invention may be continuous, rates of flow and quantities must be balanced at the inlet and at the outlet; in particular it is necessary that the cells entrained from the viscosifier 7 by the viscous product 8 be replaced by an equal quantity of cells 6 issuing from fermenter 1.

The viscous product 8 is optionally diluted with from 1 to 10 volumes of water 9 such that the viscosity may be that required to assist oil recovery.

There is recovered by physical separation, for example, by means of a membrane separator (or of a centrifuge) 10, the bacteria entrained in the viscous product issuing from the viscosifier 7. There are thus obtained, of the one part, viscous water 11 which may be immediately used for oil extraction and, of the other part, cells 12 which may be recycled to the viscosifier 7 and/or fermenter 1.

It can be appreciated why the process may be carried out in stable and continuous fashion; in effect the rate of dilution in the viscosifier 7 is controlled by the rate of production of the polysaccharides and one compensates for the rate of disappearance of the cells in the viscosifier which results from this adjustment in the balance by the rate of injection of cells of the fermenter 1 to the viscosifier 7 so that in the viscosifier, the concentration of polysaccharides remains constant, without fluctuations.

The advantage of this process is clearly apparent by comparison with that described in U.S. Pat. No. 3,485,719 where fermentation and viscosity increase take place in the same fermenter. It is thus necessary that the rate of dilution of the fermenter be equal at the same time to the rate of growth of the cells and to the rate of production of the polysaccharides. The fermentation region where these two last rates are equal is extremely narrow so that it is difficult to avoid fluctuations of the system about the equilibrium. In addition it is necessary to employ low rates of dilution of about 0.02 hr corresponding to a sojourn time of about 50 hours such that the operation of the fermenter under these conditions does not offer many advantages over discontinuous operation.

A process using two fermenters is proposed in U.S. Pat. No. 3,328,262 which may be considered as a simplification of U.S. Pat. No. 3,251,749. In a first fermenter, there is obtained growth of cells with a medium of which the substrate is essentially composed of proteins or proteinaceous extracts but comprises no or only little carbohydrate so as to avoid the production of polysaccharides. The cells thus obtained are then transferred with their growth medium into a second fermenter where the medium is enriched in carbohydrate such as to favour the production of polysaccharides. The authors specify that the medium of the second fermenter should contain nitrogeneous compositions and other nutrients such as to permit the bacteria to continue their growth such that the production of polysaccharides is not separated from the growth of the cells and is in fact returned to the preceding case despite the possibility of better control of concentration of cells in the second fermenter by the injection of cells which have been produced in the first.

According to the present invention, during the fermentation by means of Rhizobium meliloti and the production of the corresponding polysaccharides, there can be observed surprising results in using two different media, one for the growth of bacteria and the other for the production of polysaccharides.

During the use of the growth medium it can normally be ascertained that the rate of growth is exponential with time but that the rate of production of the polysaccharides is linear. For example the viscosity of the medium is only 10 centipoises (for a low rate of shearing stress) at the end of two days even though the growth of cells has already reached it plateau.

On the other hand during the use of a viscosity increase medium it has been observed that the viscosity develops in exponential fashion and its value attains several hundreds of centipoises at the end of two days.

The Example which follows permits a man skilled in the art better to understand the advantages of the present invention.

EXAMPLE

There is introduced into a first chamber of fermenter 1 a strain of Rhizobium meliloti and, continuously, a nutrient medium. This last comprises a carbohydrate substrate 2 such as described above, nitrogen salts and growth factors. This fermenter is maintained under aerobic conditions at a temperature in the region of 32° C. and the pH of the medium is approximately neutral.

At the end of about 8 hours, the fermenter reaches its equilibrium for a rate for addition of nutrient medium of 1 liter/hour, an aqueous product 3 which contains about 2 grams cells, 2 grams residual substrate and practically no polysaccharides.

This aqueous product 3 is introduced into a centrifuge 4 rotating at 5000 g: there is collected of one part the fermentation medium 5 which comprises more than 95% of the nutrient medium and about 0.2 g/l of cells and which is recycled to the fermenter and of the other part about 90% of the bacteria 6 entrained in the aqueous product 3.

Independently of the bacteria 6 recovered, there is added in continuous manner into a second chamber or viscosifier 7 12 liters by volume of nutrient medium such as that described above containing the same carbohydrate substrate as that introduced into the fermenter 1.

The pH of the medium is maintained at approximately 7.6 with a normal solution of potash. The mixture is maintained at 32° C. and air is blown in.

After a delay of about 30 hours, the concentration of polysaccharides in this second chamber 7 attains 2.5 g/l; the system is thus stabilised by drawing off the viscous product 8 at a rate of 0.5 l/h which corresponds to a sojourn time of 24 hours.

The viscosity of this product 8 is thus of about 410 centipoises for a rate of shearing stress of 5.1 per second.

In order that the process according to the present invention may be continuous, rates of flow and quantities must be balanced at the inlet and outlet; in the example given, the entrained cells from the viscosifier 7 in the viscous product 8, being 4 g/h are replaced by an equal quantity of cells 6 issuing from the fermenter 1. In the same way the rate of introduction of the solution of carbon-containing substrate 2 is equal to that of the viscous product 8 being 0.5 l/h.

The viscous product 8 is diluted with water at a rate of 2 l/h, that is to say in a ratio 4 and there is obtained a rate of flow of viscous water of 2.5 l/h containing 1 g/l of polysaccharides in which the viscosity is of 140 cp for a rate of shearing stress of 5.1 sec$^{-1}$. This viscous water can be used for the assisted recovery of oil.

In addition the viscous product 8 can be submitted to physical separation such as a centrifugation, in order to remove the entrained bacterial cells. In this operational example, there may thus be collected 4 g/h of cells which are recycled to the fermenter 1 or to the viscosifier 7.

I claim:

1. Process for continously preparing viscous water by bacterial action, which process comprises the following steps:
    (a) introducing into a first chamber containing a bacterial strain capable of excreting polysaccharides having viscosity increasing properties chosen from the genus Rhizobium, a carbohydrate substrate, nitrogeneous material in the form of mineral salts, and growth factors;
    (b) collecting from the outlet of the said first chamber an aqueous product separating the bacteria from the aqueous product;
    (c) introducing into a second chamber, by a first inlet, the bacteria recovered from step (b), and, by a second inlet, a carbohydrate substrate providing the raw material for synthesis of the polysaccharides; and
    (d) collecting from the outlet of said second chamber a viscous product at a rate approximately equal to that of the carbohydrate substrate at the inlet of the said second chamber.

2. Process according to claim 1 wherein during the said step (b) the bacteria are separated by centrifuging from said aqueous product collected.

3. Process according to claim 2 wherein the said aqueous product substantially free from bacteria is recycled to the said step (a).

4. Process according to claim 1 which also comprises the following step:
    (e) diluting the said viscous product issuing from the said step (d) with water.

5. Process according to claim 4 which further comprises the following step:
    (f) recovering by centrifuging the bacteria entrained in the product of said step (d) and recycling them to the said step (a).

6. Process according to claim 1 wherein the same carbohydrate substrate is introduced in the said steps (a) and (c).

7. Process according to claim 6 wherein the said carbohydrate substrate is chosen from the group consisting of the hexoses and their mixtures and starchy products and their hydrolysates.

8. Process according to claim 7 wherein said hexoses include glucose or fructose and said starchy products include corn or manioc.

* * * * *